United States Patent
Goodwin et al.

(10) Patent No.: US 8,293,878 B2
(45) Date of Patent: *Oct. 23, 2012

(54) METHODS AND COMPOUNDS USEFUL FOR THE PREPARATION OF SODIUM GLUCOSE CO-TRANSPORTER 2 INHIBITORS

(75) Inventors: Nicole Cathleen Goodwin, Pennington, NJ (US); Bryce Alden Harrison, Hamilton, NJ (US); Shinya Iimura, Lawrenceville, NJ (US); Ross Mabon, Princeton, NJ (US); Qiuling Song, Newark, DE (US); Wenxue Wu, Princeton, NJ (US); Jie Yan, Plainsboro, NJ (US); Haiming Zhang, Lawrenceville, NJ (US); Matthew Mangzhu Zhao, Edison, NJ (US)

(73) Assignee: Lexicon Pharmaceuticals, Inc., The Woodlands, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/207,576

(22) Filed: Aug. 11, 2011

(65) Prior Publication Data

US 2012/0095197 A1 Apr. 19, 2012

Related U.S. Application Data

(63) Continuation of application No. 12/174,722, filed on Jul. 17, 2008, now Pat. No. 8,026,347.

(60) Provisional application No. 60/952,122, filed on Jul. 26, 2007.

(51) Int. Cl.
*C07G 3/00* (2006.01)
*C07H 15/00* (2006.01)

(52) U.S. Cl. .................... 536/18.5; 536/18.6

(58) Field of Classification Search .................... None
See application file for complete search history.

(56) References Cited

U.S. PATENT DOCUMENTS

| | | | |
|---|---|---|---|
| 6,414,126 B1 | 7/2002 | Ellsworth | |
| 6,515,117 B2 | 2/2003 | Ellsworth | |
| 6,555,519 B2 | 4/2003 | Washburn | |
| 6,562,791 B1 | 5/2003 | Maurya | |
| 6,683,056 B2 | 1/2004 | Washburn | |
| 6,774,112 B2 | 8/2004 | Gougoutas | |
| 6,936,590 B2 | 8/2005 | Washburn | |
| 7,045,665 B2 | 5/2006 | Fujikura | |
| 7,053,060 B2 | 5/2006 | Fujikura | |
| 7,202,350 B2 | 4/2007 | Imamura | |
| 7,250,522 B2 | 7/2007 | Sato | |
| 7,772,378 B2 | 8/2010 | Himmelsbach | |
| 7,781,577 B2 | 8/2010 | Harrison | |
| 2010/0016422 A1 | 1/2010 | De Paul | |

OTHER PUBLICATIONS

Kanazawa et al. Polymer (2006), vol. 47, pp. 176-183.*
Davis, N.J. and Flitsch, S.L., *Tetrahedron Letters* 34(7):1181-1184 (1993).
Handlon, A.L., *Expert Opin Therapeutic Patents* 15(11):1531-1540 (2005).
Kanazawa et al., *Polymer* 47:176-183 (2006).
Search Report and Written Opinion for Corresponding International Application PCT/US2008/070250, dated Nov. 19, 2008.

* cited by examiner

*Primary Examiner* — Patrick Lewis
(74) *Attorney, Agent, or Firm* — Max Bachrach (57) ABSTRACT

Methods of synthesizing sodium glucose co-transporter 2 inhibitors, as well as compounds useful therein, are disclosed. Particular inhibitors are compounds of formula I.

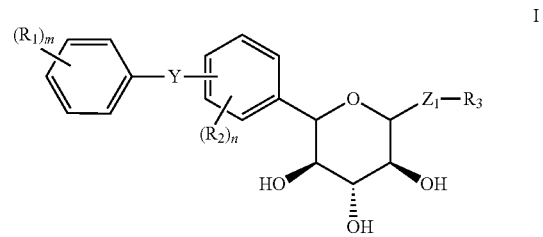

14 Claims, 4 Drawing Sheets

METHODS AND COMPOUNDS USEFUL FOR THE PREPARATION OF SODIUM GLUCOSE CO-TRANSPORTER 2 INHIBITORS

This application is a continuation of U.S. patent application Ser. No. 12/174,722, filed Jul. 17, 2008, which claims priority to U.S. provisional application No. 60/952,122, filed Jul. 26, 2008, the entireties of which are incorporated herein by reference.

1. FIELD OF THE INVENTION

This invention relates to methods of preparing inhibitors of sodium glucose co-transporter 2.

2. BACKGROUND

The sodium glucose co-transporter 2 (SGLT2) is a transporter that reabsorbs glucose from the renal filtrate and prevents the loss of glucose in the urine. Because competitive inhibitors of SGLT2 cause the renal excretion of glucose, they may be used to normalize high blood glucose levels associated with diseases such as diabetes. Handlon, A. L., *Expert Opin. Ther. Patents* 15(11):1531-1540 (2005).

In the search for new drugs that may be used to treat diabetes, a number of SGLT2 inhibitors have been disclosed. See, e.g., Handlon, supra; U.S. Pat. No. 6,515,117; U.S. patent application publication nos. US 2006/0035841, US 2004/0138439. At least one inhibitor is in clinical development as a treatment for Type 2 diabetes mellitus. See, e.g., Komoroski, B., et al., "Dapagliflozin (BMS-512148), a Selective Inhibitor of the Sodium-Glucose Uptake Transporter 2 (SGLT2), Reduces Fasting Serum Glucose and Glucose Excursion in Type 2 Diabetes Mellitus Patients Over 14 Days" *American Diabetes Assn. 67th Scientific Sessions*, Abstract 0188-OR (2007).

3. SUMMARY OF THE INVENTION

This invention encompasses methods of preparing certain inhibitors of SGLT2, as well as compounds useful therein.

One embodiment of the invention encompasses a method of preparing compounds of formula I:

the substitutes of which are defined herein, and salts thereof, which comprises contacting a compound of formula II:

with a base under suitable conditions.

Also encompassed by the invention are various intermediates useful in the preparation of SGLT2 inhibitors, including compounds of formula I.

4. BRIEF DESCRIPTION OF THE FIGURES

Certain aspects of the invention may be understood with reference to the attached figures.

5. DETAILED DESCRIPTION

Novel compounds that inhibit the sodium glucose co-transporter 2 (SGLT2) were recently disclosed. See U.S. provisional application Nos. 60/848,156, filed Sep. 29, 2006, and 60/905,714, filed Mar. 8, 2007. This invention is based, in part, on the discovery of new methods of preparing those compounds. Particular methods of the invention allow for the compounds' large-scale manufacture.

5.1. Definitions

Unless otherwise indicated, the term "alkenyl" means a straight chain, branched and/or cyclic hydrocarbon having from 2 to 20 (e.g., 2 to 10 or 2 to 6) carbon atoms, and including at least one carbon-carbon double bond. Representative alkenyl moieties include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl and 3-decenyl.

Unless otherwise indicated, the term "alkoxy" means an —O-alkyl group. Examples of alkoxy groups include, but are not limited to, —OCH$_3$, —OCH$_2$CH$_3$, —O(CH$_2$)$_2$CH$_3$, —O(CH$_2$)$_3$CH$_3$, —O(CH$_2$)$_4$CH$_3$, and —O(CH$_2$)$_5$CH$_3$.

Unless otherwise indicated, the term "alkyl" means a straight chain, branched and/or cyclic ("cycloalkyl") hydrocarbon having from 1 to 20 (e.g., 1 to 10 or 1 to 4) carbon atoms. Alkyl moieties having from 1 to 4 carbons are referred to as "lower alkyl." Examples of alkyl groups include, but are not limited to, methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl and dodecyl. Cycloalkyl moieties may be monocyclic or multicyclic, and examples include cyclopropyl, cyclobutyl, cyclopentyl, cyclohexyl, and adamantyl. Additional examples of alkyl moieties have linear, branched and/or cyclic portions (e.g., 1-ethyl-4-methyl-cyclohexyl). The term "alkyl" includes saturated hydrocarbons as well as alkenyl and alkynyl moieties.

Unless otherwise indicated, the term "alkylaryl" or "alkyl-aryl" means an alkyl moiety bound to an aryl moiety.

Unless otherwise indicated, the term "alkylheteroaryl" or "alkyl-heteroaryl" means an alkyl moiety bound to a heteroaryl moiety.

Unless otherwise indicated, the term "alkylheterocycle" or "alkyl-heterocycle" means an alkyl moiety bound to a heterocycle moiety.

Unless otherwise indicated, the term "alkynyl" means a straight chain, branched or cyclic hydrocarbon having from 2 to 20 (e.g., 2 to 20 or 2 to 6) carbon atoms, and including at least one carbon-carbon triple bond. Representative alkynyl moieties include acetylenyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl, 1-heptynyl, 2-heptynyl, 6-heptynyl, 1-octynyl, 2-octynyl, 7-octynyl, 1-nonynyl, 2-nonynyl, 8-nonynyl, 1-decynyl, 2-decynyl and 9-decynyl.

Unless otherwise indicated, the term "aryl" means an aromatic ring or an aromatic or partially aromatic ring system composed of carbon and hydrogen atoms. An aryl moiety may comprise multiple rings bound or fused together. Examples of aryl moieties include, but are not limited to, anthracenyl, azulenyl, biphenyl, fluorenyl, indan, indenyl, naphthyl, phenanthrenyl, phenyl, 1,2,3,4-tetrahydro-naphthalene, and tolyl.

Unless otherwise indicated, the term "arylalkyl" or "aryl-alkyl" means an aryl moiety bound to an alkyl moiety.

Unless otherwise indicated, the terms "halogen" and "halo" encompass fluorine, chlorine, bromine, and iodine.

Unless otherwise indicated, the term "heteroalkyl" refers to an alkyl moiety (e.g., linear, branched or cyclic) in which at least one of its carbon atoms has been replaced with a heteroatom (e.g., N, O or S).

Unless otherwise indicated, the term "heteroaryl" means an aryl moiety wherein at least one of its carbon atoms has been replaced with a heteroatom (e.g., N, O or S). Examples include, but are not limited to, acridinyl, benzimidazolyl, benzofuranyl, benzoisothiazolyl, benzoisoxazolyl, benzoquinazolinyl, benzothiazolyl, benzoxazolyl, furyl, imidazolyl, indolyl, isothiazolyl, isoxazolyl, oxadiazolyl, oxazolyl, phthalazinyl, pyrazinyl, pyrazolyl, pyridazinyl, pyridyl, pyrimidinyl, pyrimidyl, pyrrolyl, quinazolinyl, quinolinyl, tetrazolyl, thiazolyl, and triazinyl.

Unless otherwise indicated, the term "heteroarylalkyl" or "heteroaryl-alkyl" means a heteroaryl moiety bound to an alkyl moiety.

Unless otherwise indicated, the term "heterocycle" refers to an aromatic, partially aromatic or non-aromatic monocyclic or polycyclic ring or ring system comprised of carbon, hydrogen and at least one heteroatom (e.g., N, O or S). A heterocycle may comprise multiple (i.e., two or more) rings fused or bound together. Heterocycles include heteroaryls. Examples include, but are not limited to, benzo[1,3]dioxolyl, 2,3-dihydro-benzo[1,4]dioxinyl, cinnolinyl, furanyl, hydantoinyl, morpholinyl, oxetanyl, oxiranyl, piperazinyl, piperidinyl, pyrrolidinonyl, pyrrolidinyl, tetrahydrofuranyl, tetrahydropyranyl, tetrahydropyridinyl, tetrahydropyrimidinyl, tetrahydrothiophenyl, tetrahydrothiopyranyl and valerolactamyl.

Unless otherwise indicated, the term "heterocyclealkyl" or "heterocycle-alkyl" refers to a heterocycle moiety bound to an alkyl moiety.

Unless otherwise indicated, the term "heterocycloalkyl" refers to a non-aromatic heterocycle.

Unless otherwise indicated, the term "heterocycloalkylalkyl" or "heterocycloalkyl-alkyl" refers to a heterocycloalkyl moiety bound to an alkyl moiety.

Unless otherwise indicated, the term "pharmaceutically acceptable salts" refers to salts prepared from pharmaceutically acceptable non-toxic acids or bases including inorganic acids and bases and organic acids and bases. Suitable pharmaceutically acceptable base addition salts include, but are not limited to, metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts. Others are well-known in the art. See, e.g., *Remington's Pharmaceutical Sciences*, 18th ed. (Mack Publishing, Easton Pa.: 1990) and *Remington: The Science and Practice of Pharmacy*, 19th ed. (Mack Publishing, Easton Pa.: 1995).

Unless otherwise indicated, the term "stereoisomeric mixture" encompasses racemic mixtures as well as stereomerically enriched mixtures (e.g., R/S=30/70, 35/65, 40/60, 45/55, 55/45, 60/40, 65/35 and 70/30).

Unless otherwise indicated, the term "stereomerically pure" means a composition that comprises one stereoisomer of a compound and is substantially free of other stereoisomers of that compound. For example, a stereomerically pure composition of a compound having one stereocenter will be substantially free of the opposite stereoisomer of the compound. A stereomerically pure composition of a compound having two stereocenters will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, greater than about 97% by weight of one stereoisomer of the compound and less than about 3% by weight of the other stereoisomers of the compound, or greater than about 99% by weight of one stereoisomer of the compound and less than about 1% by weight of the other stereoisomers of the compound.

Unless otherwise indicated, the term "substituted," when used to describe a chemical structure or moiety, refers to a derivative of that structure or moiety wherein one or more of its hydrogen atoms is substituted with a chemical moiety or functional group such as, but not limited to, alcohol, aldehyde, alkoxy, alkanoyloxy, alkoxycarbonyl, alkenyl, alkyl (e.g., methyl, ethyl, propyl, t-butyl), alkynyl, alkylcarbonyloxy (—OC(O)alkyl), amide (—C(O)NH-alkyl- or -alkyl-NHC(O)alkyl), amidinyl (—C(NH)NH-alkyl- or —C(NR)NH$_2$), amine (primary, secondary and tertiary such as alkylamino, arylamino, arylalkylamino), aroyl, aryl, aryloxy, azo, carbamoyl (—NHC(O)O-alkyl- or —OC(O)NH-alkyl), carbamyl (e.g., CONH$_2$, as well as CONH-alkyl, CONH-aryl, and CONH-arylalkyl), carbonyl, carboxyl, carboxylic acid, carboxylic acid anhydride, carboxylic acid chloride, cyano, ester, epoxide, ether (e.g., methoxy, ethoxy), guanidino, halo, haloalkyl (e.g., —CCl$_3$, —CF$_3$, —C(CF$_3$)$_3$), heteroalkyl, hemiacetal, imine (primary and secondary), isocyanate, isothiocyanate, ketone, nitrile, nitro, oxo, phosphodiester, sulfide, sulfonamido (e.g., SO$_2$NH$_2$), sulfone, sulfonyl (including alkylsulfonyl, arylsulfonyl and arylalkylsulfonyl), sulfoxide, thiol (e.g., sulfhydryl, thioether) and urea (—NHCONH-alkyl-).

Unless otherwise indicated, the term "include" has the same meaning as "include, but are not limited to," and the term "includes" has the same meaning as "includes, but is not limited to." Similarly, the term "such as" has the same meaning as the term "such as, but not limited to."

Unless otherwise indicated, one or more adjectives immediately preceding a series of nouns is to be construed as applying to each of the nouns. For example, the phrase "optionally substituted alky, aryl, or heteroaryl" has the same meaning as "optionally substituted alky, optionally substituted aryl, or optionally substituted heteroaryl."

It should be noted that a chemical moiety that forms part of a larger compound may be described herein using a name commonly accorded it when it exists as a single molecule or a name commonly accorded its radical. For example, the terms "pyridine" and "pyridyl" are accorded the same meaning when used to describe a moiety attached to other chemical moieties. Thus, the two phrases "XOH, wherein X is pyridyl" and "XOH, wherein X is pyridine" are accorded the same meaning, and encompass the compounds pyridin-2-ol, pyridin-3-ol and pyridin-4-ol.

It should also be noted that if the stereochemistry of a structure or a portion of a structure is not indicated with, for example, bold or dashed lines, the structure or the portion of the structure is to be interpreted as encompassing all stereoisomers of it. Moreover, any atom shown in a drawing with unsatisfied valences is assumed to be attached to enough hydrogen atoms to satisfy the valences. In addition, chemical bonds depicted with one solid line parallel to one dashed line encompass both single and double (e.g., aromatic) bonds, if valences permit.

5.2. Methods

This invention encompasses methods of preparing compounds of formula I:

and salts and co-crystals thereof, wherein: Y is O, S, NR$_4$, or C(R$_4$)$_2$; Z$_1$ is O, S, SO, or SO$_2$; each R$_1$ is independently hydrogen, halogen, cyano, OR$_{1A}$, SR$_{1A}$, or optionally substituted alkyl; each R$_{1A}$ is independently hydrogen or optionally substituted alkyl or aryl; each R$_2$ is independently hydrogen, halogen, cyano, OR$_{2A}$, SR$_{2A}$, or optionally substituted alkyl; each R$_{2A}$ is independently hydrogen or optionally substituted alkyl or aryl; R$_3$ is optionally substituted alkyl, aryl or heterocycle; each R$_4$ is independently hydrogen or optionally substituted alkyl or aryl; n is 1-3; and m is 1-3.

A particular approach is shown below in Scheme 1:

wherein each P$_1$ is independently a hydroxyl protecting group stable under acidic conditions. In this approach, a compound of formula II(a) is oxidized to provide a compound of formula II, which is then contacted with a base to afford the compound of formula I. Suitable oxidation conditions are known in the art, and include the use of peroxy compounds, such as m-chlorophenylperacid, peracetic acid, oxone, a mixture of hydrogen peroxide or its complex (e.g., urea hydrogen peroxide) and acid anhydride (e.g., phthalic anhydride). Suitable bases are also known in the art, and include alkoxides, hydroxide, carbonates and amines.

Of course, potentially reactive moieties encompassed by the definitions of various moieties (e.g., R$_1$-R$_3$) provided herein may be protected using methods known in the art. Moreover, the final product may undergo further reactions known in the art to afford other compounds encompassed by formula I. The final product may also be crystallized. In one method, the product is co-crystallized with an amino acid (e.g., L-phenylalanine, L-phenylglycine, L-arginine).

With regard to all of the generic structures and reactions disclosed herein (e.g., in Schemes 1-3), where applicable, certain embodiments of the invention are such that Y is C(R$_4$)$_2$. In others, Z$_1$ is S, SO or SO$_2$. In others, each P$_1$ is independently C(O)R$_5$, wherein each R$_5$ is independently alkyl, aryl, alkylaryl, or arylalkyl. Examples of P$_1$ include acetyl, benzoyl and pivaloyl. In other embodiments, R$_1$ is OR$_{1A}$ and R$_{1A}$ is, for example, optionally substituted lower alkyl. In others, $R_2$ is halogen. In others, $R_3$ is lower alkyl (e.g., methyl or ethyl). In others, $R_4$ is hydrogen. In others, m is 1. In others, n is 1.

Figure 1:
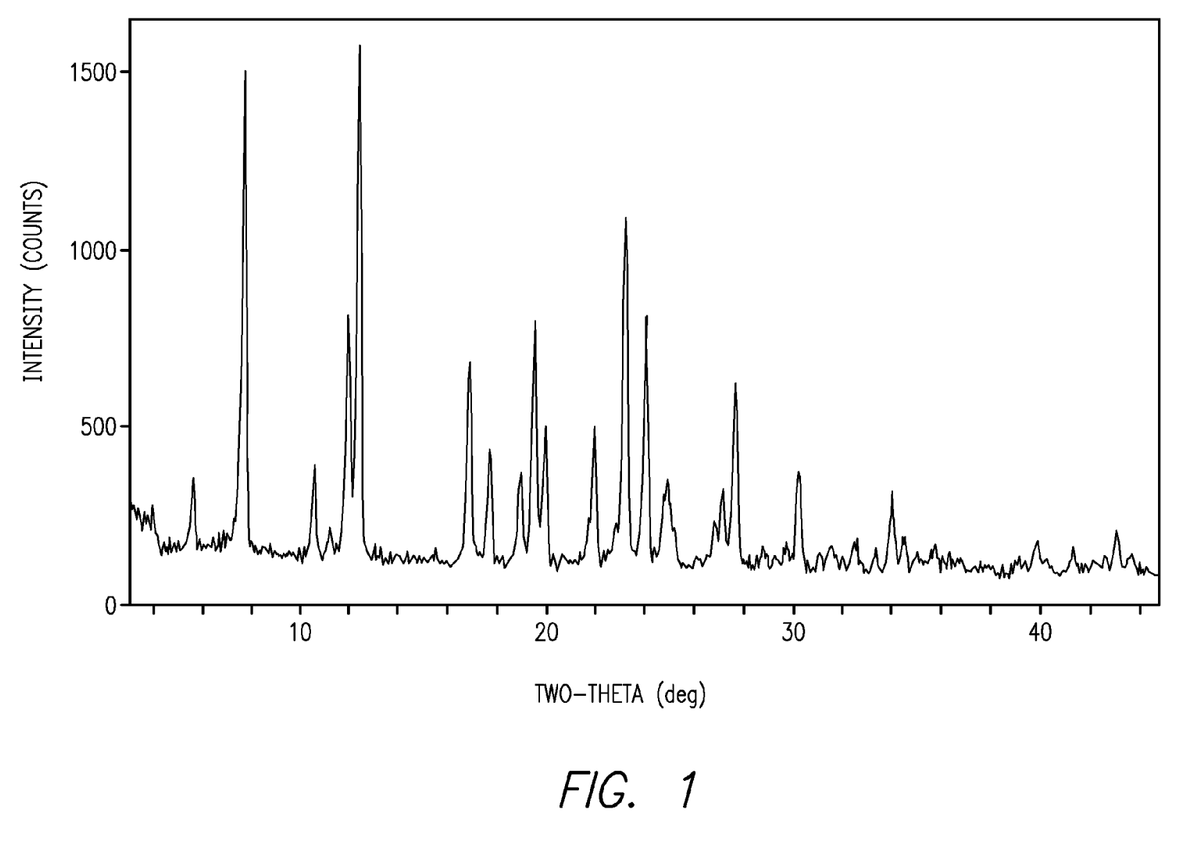
FIG. 1 is a X-ray diffraction pattern of a crystalline solid form of (2S,3S,4R,5S,6R)-2-(4-chloro-3-(4-ethoxybenzyl)phenyl)-6-(methylthio)tetrahydro-2H-pyran-3,4,5-triyl triacetate. The spectrum was obtained using a Rigaku MiniFlex diffractometer (Cu (1.54060 Å) radiation).

In one embodiment, Y is $CH_2$, $Z_1$ is S or $SO_2$, $R_1$ is ethoxy, $R_2$ is chloro, and $R_3$ is methyl. For example, in a particular method, the compound of formula I is of the formula:

In another embodiment, Y is $CH_2$, $Z_1$ is S or $SO_2$, $R_1$ is ethoxy, $R_2$ is chloro, and $R_3$ is ethyl. For example, in a particular method, the compound of formula I is of the formula:

In a particular embodiment, the compound of formula II(a) is of formula II(b), which can be prepared as shown below in Scheme 2:

wherein X is bromine, iodine, alkanesulfoxy, or alkoxysulfoxy. Suitable reaction conditions are known in the art. For example, basic conditions (e.g., the use of a base such as N,N-diisopropyl ethylamine) can be used. In one method, the compound of formula II(b) is of the formula:

A specific compound of formula II(b) is (2S,3S,4R,5S,6R)-2-(4-chloro-3-(4-ethoxybenzyl)phenyl)-6-(methylthio)tetrahydro-2H-pyran-3,4,5-triyl triacetate:

A particular crystalline form of this compound has a melting point of about 156° C. as measured by differential scanning calorimetry (DSC) (onset temperature). The form provides a X-ray powder diffraction (XRPD) pattern with peaks at one or more of about 7.7, 11.9, 12.4, 16.9, 19.5, 19.9, 21.9, 23.2, 24.1, and/or 27.7 degrees 2θ. As those skilled in the art are well aware, the relative intensities of peaks in a X-ray diffraction pattern of a crystalline form can vary depending on how the sample is prepared and how the data is collected. With this in mind, an example of a XRPD pattern of this crystalline form is provided in FIG. 1.

In general, compounds of formula II(a) can be prepared by the approach shown below in Scheme 3:

wherein: each P$_2$ is independently a hydroxyl protecting group stable under acidic conditions, or both P$_2$s are taken together to provide a single protecting group; X' is chlorine, bromine or iodine; and X" is a leaving group (e.g., amino, alkoxyamino, hydroxy, halogen, alkoxy, phenoxy, carboxy, sulfoxy). In particular methods, each P$_2$ is independently C(O)R$_6$, or both P$_2$s are taken together to provide C(R$_6$)$_2$, wherein each R$_6$ is independently alkyl, aryl, alkylaryl, or arylalkyl.

In this approach, the compound of formula II(a) is obtained by contacting a compound of formula II(d) with reagents and reaction conditions that will depend on the nature of Z$_2$. For example, the compound of formula II(d) can be contacted with a Lewis acid (e.g., trimethylsilyl trifluoromethanesulfonate) and thiourea to obtain a compound wherein Z$_2$ is S (e.g., of formula II(c), shown above in Scheme 2). The compound of formula II(d) can be contacted with a hydroxyl compound under acidic conditions to afford a compound wherein Z$_2$ is O.

Compounds of formula II(d) can be obtained by contacting a compound of formula II(e) with P$_1$—X''' under suitable reaction conditions, wherein X''' is chlorine, bromine, iodine, alkylcarboxy, alkanesulfoxy, or alkoxysulfoxy. Suitable reaction conditions are known in the art. For example, the reaction may be catalyzed by a base, such as pyridine. In a particular embodiment, the compound of formula II(d) is of the formula:

and the salt of P$_1$ is, for example, acyl chloride or acetic anhydride.

Compounds of formula II(e) can be prepared by contacting a compound of formula III(a) with an acid under conditions sufficient to provide the compound of formula II(e). Suitable acids are known in the art, and include acetic acid, hydrochloric acid, sulfuric acid, phosphoric acid, methanesulfonic acid, and toluenesulfonic acid.

Figure 2:
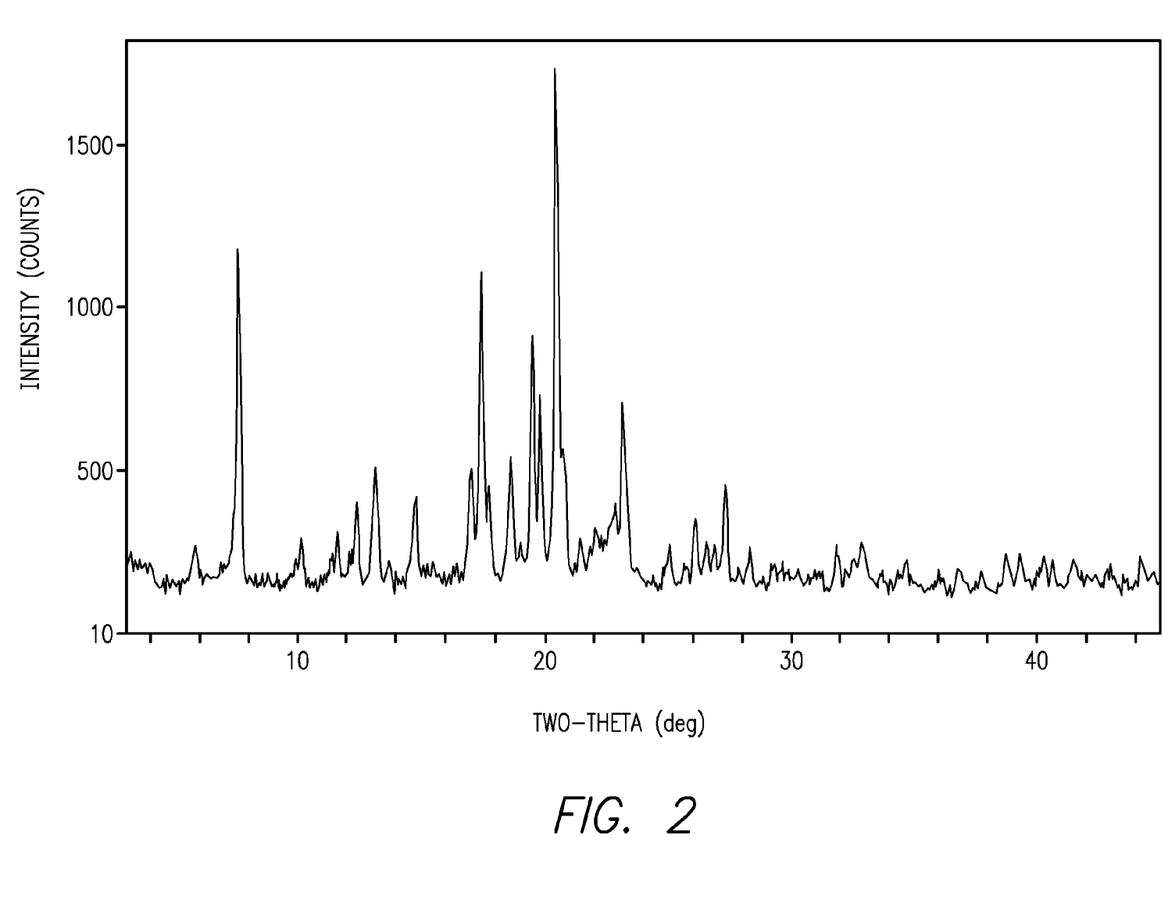
FIG. 2 is a X-ray diffraction pattern of a crystalline solid form of (4-chloro-3-(4-ethoxybenzyl)phenyl)((3aS,5R,6S,6aS)-6-hydroxy-2,2-dimethyltetrahydrofuro[2,3-d][1,3]dioxol-5-yl)methanone. The spectrum was obtained using a Rigaku MiniFlex diffractometer (Cu (1.54060 Å) radiation).

Compounds of formula III(a) can be prepared by reducing a compound of formula III(b). Suitable reducing conditions are known in the art, and include the use of cerium chloride and sodium borohydride, a borane complex, enzymatic reduction, and hydrogenation or transfer hydrogenation. In a particular embodiment, the compound of formula III(b) is of the formula:

A specific compound of formula III(b) is (4-chloro-3-(4-ethoxybenzyl)phenyl)((3aS,5R,6S,6aS)-6-hydroxy-2,2-dimethyltetrahydrofuro[2,3-d][1,3]dioxol-5-yl)methanone:

A particular crystalline form of this compound has a melting point of about 113° C. as measured by DSC (onset temperature). The form provides a XRPD pattern with peaks at one or more of about 7.6, 13.2, 17.0, 17.4, 18.6, 19.5, 20.5, 20.8 and/or 23.2 degrees 2θ. An example of a XRPD pattern of this crystalline form is provided in FIG. 2.

Compounds of formula III(b) can be prepared by coupling a compound of formula IV with a compound of formula V. Suitable coupling conditions are known in the art, and include the use of metalating (e.g., magnesium or lithium) or transmetalating agents such as magnesium reagents (e.g., alkyl magnesium halide, dialkyl magnesium, lithium trialkyl magnesium halide) and organolithium reagents (e.g., n-butyl lithium, sec-butyl lithium, t-butyl lithium). Thus, compounds of formula III(b) can be prepared using compounds of formula IV(a):

under suitable conditions, wherein M is an appropriate metal, such as Na, K, Li, or Mg, X' is Cl, Br, or I, and p is 0, 1, or 2, depending on the metal.

Figure 3:
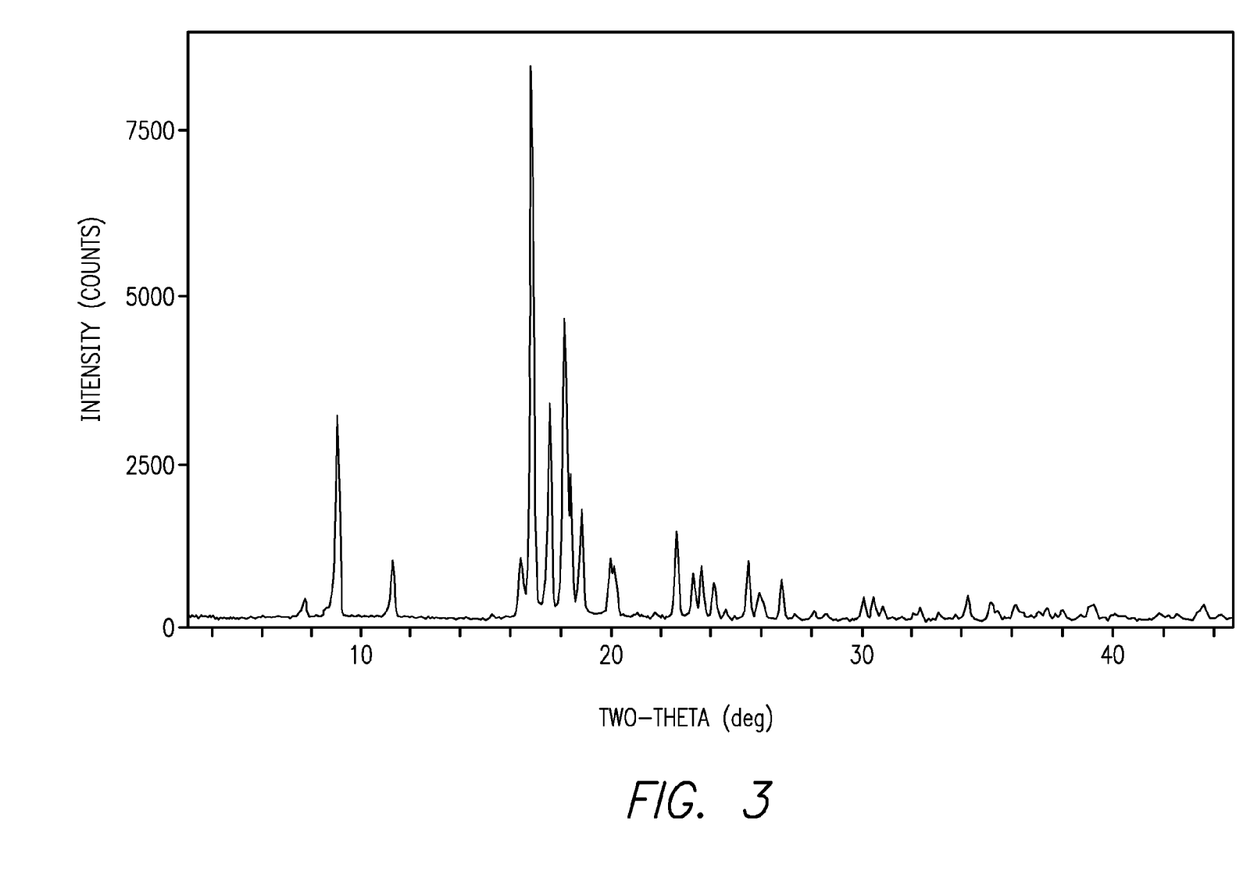
FIG. 3 is a X-ray diffraction pattern of a crystalline solid form of ((3aS,5R,6S,6aS)-6-hydroxy-2,2-dimethyltetrahydrofuro[2,3-d][1,3]dioxol-5-yl)(morpholino)methanone. The spectrum was obtained using a Rigaku MiniFlex diffractometer (Cu (1.54060 Å) radiation).

In a particular method, the compound of formula V is such that X" is amino (e.g., morpholino). A specific compound of formula V is ((3aS,5R,6S,6aS)-6-hydroxy-2,2-dimethyltetrahydrofuro[2,3-d][1,3]dioxol-5-yl)(morpholino)methanone:

A particular crystalline form of this compound has a melting point of about 136° C. as measured by DSC (onset temperature). The form provides a XRPD pattern with peaks at one or more of about 9.0, 16.9, 17.6, 18.2, 18.4, 18.8 and/or 22.7 degrees 2θ. An example of a XRPD pattern of this crystalline form is provided in FIG. 3.

This particular compound of formula V can be prepared by approaches such as that shown below in Scheme 4:

Scheme 4

Suitable reaction conditions are known in the art, and include those described below in the Examples. In general, L-(−)-xylose is cyclized under conditions sufficient to provide compound 1, which is then oxidized to provide compound 2, which is then contacted with morpholine under conditions sufficient to provide ((3aS,5R,6S,6aS)-6-hydroxy-2,2-dimethyltetrahydrofuro[2,3-d][1,3]dioxol-5-yl)(morpholino)methanone. This invention encompasses compounds of formulae 1 and 2, including crystalline forms thereof.

Figure 4:
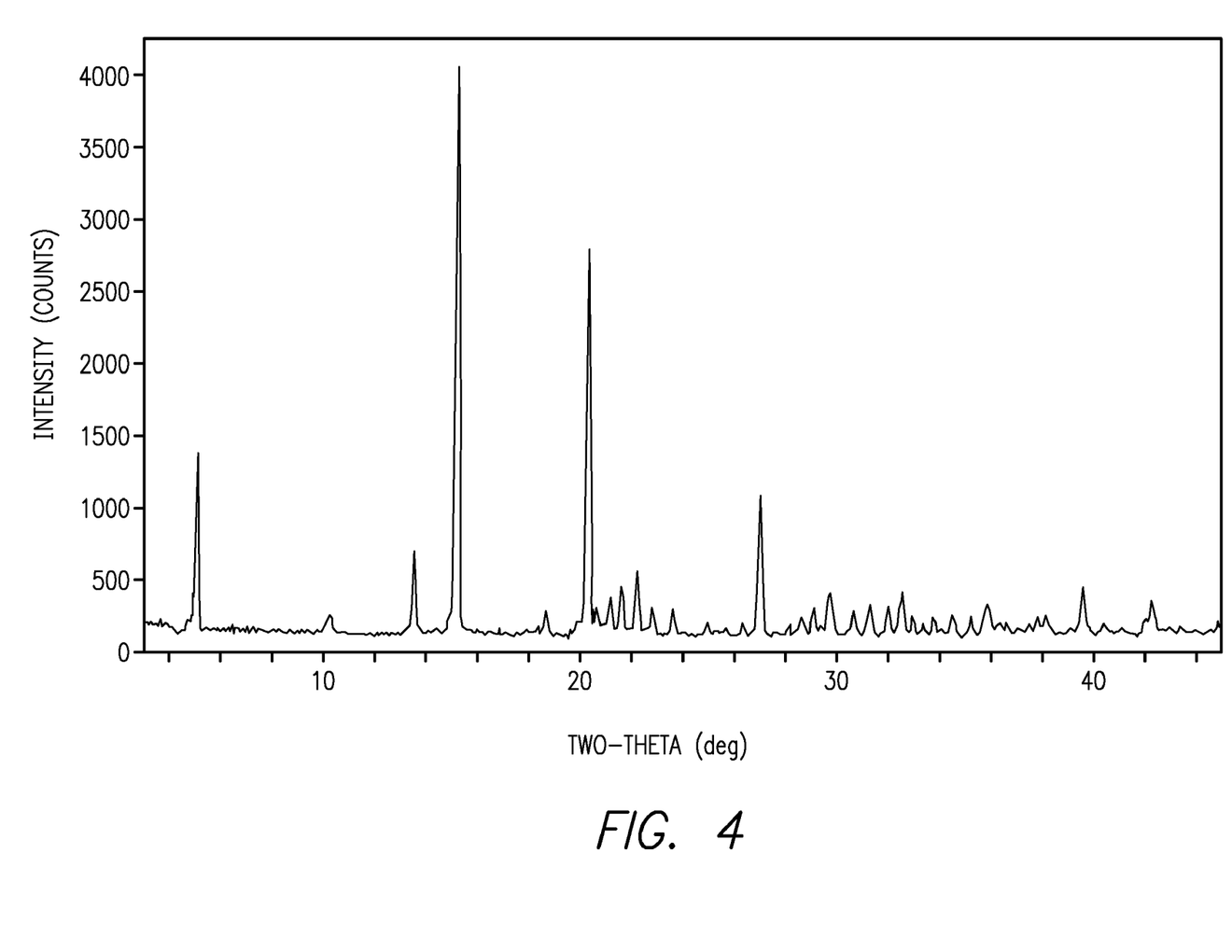
FIG. 4 is a X-ray diffraction pattern of a crystalline solid form of 1-chloro-2-(4-ethoxybenzyl)-4-iodobenzene. The spectrum was obtained using a Rigaku MiniFlex diffractometer (Cu (1.54060 Å) radiation).

Returning to Scheme 3, in a particular method of the invention, the compound of formula IV is of the formula:

A specific compound of formula IV is 1-chloro-2-(4-ethoxybenzyl)-4-iodobenzene:

A particular crystalline form of this compound has a melting point of about 65° C. (as determined by m.p. apparatus). The form provides a XRPD pattern with peaks at one or more of about 5.1, 13.5, 15.2, 20.3, 22.2 and/or 27.0 degrees 2θ. An example of a XRPD pattern of this crystalline form is provided in FIG. 4.

Particular compounds of formula IV(a) include those of the formula:

More particular compounds are of the formula:

Specific compounds of formula IV(a) are (4-chloro-3-(4-ethoxybenzyl)phenyl)magnesium iodide and (4-chloro-3-(4-ethoxybenzyl)phenyl)magnesium chloride, shown below:

Compounds of formulae IV and V can be prepared by methods such as those disclosed below, as well as methods known in the art. See, e.g., U.S. Pat. No. 6,515,117; Davis, N. J., et al., *Tetrahedron Letters* 34(7):1181-4 (1993).

6. EXAMPLES

Aspects of this invention can be understood from the following examples, which do not limit its scope.

6.1. Synthesis of ((3aS,5R,6S,6aS)-6-hydroxy-2,2-dimethyltetrahydrofuro[2,3-d][1,3]-dioxol-5-yl)(morpholino)methanone To a 12 L three-necked round bottom flask with mechanical stirrer, rubber septum with temperature probe and gas bubbler was charged L-(−)-xylose (504.40 g, 3.360 mol), acetone (5 L, reagent grade) and anhydrous MgSO$_4$ powder (811.23 g, 6.740 mol/2.0 equiv). The suspension was set stirring at ambient and then concentrated H$_2$SO$_4$ (50 mL, 0.938 mol/0.28 equiv) was added. A slow mild exotherm was noticed (temperature rose to 24° C. over about 1 hr) and the reaction was allowed to stir at ambient overnight. After 16.25 hours, TLC suggested all L-xylose had been consumed, with the major product being the bis-acetonide along with some (3aS,5S,6R,6aS)-5-(hydroxymethyl)-2,2-dimethyltetrahydrofuro[2,3-d][1,3]dioxol-6-ol. The reaction mixture was filtered and the collected solids were washed twice with acetone (500 mL per wash). The stirring yellow filtrate was neutralized with concentrated NH$_4$OH solution (39 mL) to pH=8.7. After stirring for 10 min, the suspended solids were removed by filtration. The filtrate was concentrated to afford crude bis-acetonide intermediate as a yellow oil (725.23 g). The yellow oil was suspended in 2.5 L water stirring in a 5 L three-necked round bottom flask with mechanical stirrer, rubber septum with temperature probe and gas bubbler. The pH was adjusted from 9 to 2 with 1N aq. HCl (142 mL) and stirred at room temperature for 6 h until GC showed sufficient conversion of the bis-acetonide intermediate to (3aS,5S,6R,6aS)-5-(hydroxymethyl)-2,2-dimethyltetrahydrofuro[2,3-d][1,3]dioxol-6-ol. The reaction was neutralized by the addition of 50% w/w aq. K$_2$HPO$_4$ until pH=7. The solvent was then evaporated and ethyl acetate (1.25 L) was added to give a white suspension which was filtered. The filtrate was concentrated in vacuo to afford an orange oil which was dissolved in 1 L methyl tert-butyl ether. This solution had KF 0.23 wt % water and was concentrated to afford (3aS,5S,6R,6aS)-5-(hydroxymethyl)-2,2-dimethyltetrahydrofuro[2,3-d][1,3]dioxol-6-ol as an orange oil (551.23 g, 86% yield, 96.7 area % pure by GC). $^1$H NMR (400 MHz, DMSO-d$_6$) δ 1.22 (s, 3 H) 1.37 (s, 3H) 3.51 (dd, J=11.12, 5.81 Hz, 1H) 3.61 (dd, J=11.12, 5.05 Hz, 1H) 3.93-4.00 (m, 1H) 3.96 (s, 1H) 4.36 (d, J=3.79 Hz, 1H) 4.86 (br. s., 2H) 5.79 (d, J=3.54 Hz, 1H). $^{13}$C NMR (101 MHz, DMSO-d$_6$) δ 26.48, 27.02, 59.30, 73.88, 81.71, 85.48, 104.69, 110.73.

To a solution of (3aS,5S,6R,6aS)-5-(hydroxymethyl)-2,2-dimethyltetrahydrofuro[2,3-d][1,3]dioxol-6-ol (25.0 g, 131 mmol) in acetone (375 mL, 15×) and H$_2$O (125 mL, 5×) was added NaHCO$_3$ (33.0 g, 3.0 equiv), NaBr (2.8 g, 20 mol %) and TEMPO (0.40 g, 2 mol %) at 20° C. The mixture was cooled to 0-5° C. and solid trichloroisocyanuric acid (TCCA, 30.5 g, 1.0 equiv) was then added in portions. The suspension was stirred at 20° C. for 24 h. Methanol (20 mL) was added and the mixture was stirred at 20° C. for 1 h. A white suspension was formed at this point. The mixture was filtered, washed with acetone (50 mL, 2×). The organic solvent was removed under vacuum and the aqueous layer was extracted with EtOAc (300 mL, 12× x3) and the combined organic layers were concentrated to afford an oily mixture with some solid residue. Acetone (125 mL, 5×) was added and the mixture was filtered. The acetone solution was then concentrated to afford the desired acid ((3aS,5R,6S,6aS)-6-hydroxy-2,2-dimethyltetrahydrofuro[2,3-d][1,3]dioxole-5-carboxylic acid) as a yellow solid (21.0 g, 79%). $^1$H NMR (methanol-d$_4$), δ 6.00 (d, J=3.2 Hz, 1H), 4.72 d, J=3.2 Hz, 1H), 4.53 (d, J=3.2 Hz, 1H), 4.38 (d, J=3.2 Hz, 1H), 1.44 (s, 3H), 1.32 (s, 3H).

To a solution of (3aS,5R,6S,6aS)-6-hydroxy-2,2-dimethyltetrahydrofuro[2,3-d][1,3]dioxole-5-carboxylic acid (5.0 g, 24.5 mmol) in THF (100 mL, 20×) was added TBTU (11.8 g, 1.5 equiv), N-methylmorpholine (NMM, 4.1 mL, 1.5 equiv) and the mixture was stirred at 20° C. for 30 min. Morpholine (3.2 mL, 1.5 equiv) was then added, and the reaction mixture was stirred at 20° C. for an additional 6 h. The solid was filtered off by filtration and the cake was washed with THF (10 mL, 2× x2). The organic solution was concentrated under vacuum and the residue was purified by silica gel column chromatography (hexanes:EtOAc, from 1:4 to 4:1) to afford 4.3 g of the desired morpholine amide (64%) as a white solid. $^1$H NMR (CDCl$_3$), δ 6.02 (d, J=3.2 Hz, 1H), 5.11 (br s, 1H), 4.62 (d, J=3.2 Hz, 1H), 4.58 (d, J=3.2 Hz, 1H), 3.9-3.5 (m, 8H), 1.51 (s, 3H), 1.35 (s, 3H).

6.2. Alternative synthesis of ((3aS,5R,6S,6aS)-6-hydroxy-2,2-dimethyltetrahydrofuro[2,3-d][1,3]dioxol-5-yl)(morpholino)methanone A solution of the diol (3aS,5S,6R,6aS)-5-(hydroxymethyl)-2,2-dimethyltetrahydrofuro[2,3-d][1,3]dioxol-6-ol in acetonitrile (5.38 kg, 65% w/w, 3.50 kg active, 18.40 mol), acetonitrile (10.5 L) and TEMPO (28.4 g, 1 mol %) were added to a solution of K$_2$HPO$_4$ (0.32 kg, 1.84 mol) and KH$_2$PO$_4$ (1.25 kg, 9.20 mol) in water (10.5 L). A solution of NaClO$_2$ (3.12 kg, 80% w/w, 27.6 mole, 1.50 eq) in water (7.0 L) and a solution of K$_2$HPO$_4$ (2.89 kg, 0.90 eq) in water (3.0 L) were prepared with cooling. Bleach (3.0 L, approximate 6% household grade) was mixed with the K$_2$HPO$_4$ solution. Approximately 20% of the NaClO$_2$ solution (1.6 L) and bleach/K$_2$HPO$_4$ solution (400 mL, ~1 mol %) were added. The remainders of the two solutions were added simultaneously. The reaction mixture turned dark red brown and slow exotherm was observed. The addition rate of the NaClO$_2$ solution was about 40 mL/min (3-4 h addition) and the addition rate for the bleach/K$_2$HPO$_4$ solution was about 10-12 mL/min (10 hr addition) while maintaining the batch at 15-25° C. Additional charges of TEMPO (14.3 g, 0.5 mol %) were performed every 5-6 hr until the reaction went to completion (usually two charges are sufficient). Nitrogen sweep of the headspace to a scrubber with aqueous was performed to keep the green-yellowish gas from accumulating in the vessel. The reaction mixture was cooled to <10° C. and quenched with Na$_2$SO$_3$ (1.4 kg, 0.6 eq) in three portions over 1 hr. The reaction mixture was then acidified with H$_3$PO$_4$ until pH reached 2.0-2.1 (2.5-2.7 L) at 5-15° C. The layers were separated and the aqueous layer was extracted with acetonitrile (10.5 L×3). The combined organic layer was concentrated under vacuo (~100-120 torr) at <35° C. (28-32° C. vapor, 45-50° C. bath) to low volume (~6-7 L) and then flushed with acetonitrile (40 L) until KF of the solution reached <1% when diluted to volume of about 12-15 L with acetonitrile. Morpholine (1.61 L, 18.4 mol, 1.0 eq) was added over 4-6 h and the slurry was aged overnight under nitrogen. The mixture was cooled to 0-5° C. and aged for 3 hours then filtered. The filter cake was washed with acetonitrile (10 L). Drying under flowing nitrogen gave 4.13 kg of the morpholine salt of ((3aS,5R,6S,6aS)-6-hydroxy-2,2-dimethyltetrahydrofuro[2,3-d][1,3]dioxole-5-carboxylic acid as a white solid (92-94% pure based on $^1$H NMR with 1,4-dimethoxybenzene as the internal standard), 72-75% yield corrected for purity. $^1$H NMR (D$_2$O) δ 5.96 (d, J=3.6 Hz, 1H), 4.58 (d, J=3.6 Hz, 1H), 4.53 (d, J=3.2 Hz, 1H), 4.30 (d, J=3.2 Hz, 1H), 3.84 (m, 2H), 3.18 (m, 2H), 1.40 (s, 1H), 1.25 (s, 1H). $^{13}$H NMR (D$_2$O) δ 174.5, 112.5, 104.6, 84.2, 81.7, 75.0, 63.6, 43.1, 25.6, 25.1.

The morpholine salt of ((3aS,5R,6S,6aS)-6-hydroxy-2,2-dimethyltetrahydrofuro[2,3-d][1,3]dioxole-5-carboxylic acid (7.85 kg, 26.9 mol), morpholine (2.40 L, 27.5 mol) and boric acid (340 g, 5.49 mol, 0.2 eq) were added to toluene (31 L). The resulting slurry was degassed and heated at reflux with a Dean-Stark trap under nitrogen for 12 h and then cooled to room temperature. The mixture was filtered to remove insolubles and the filter cake washed with toluene (5 L). The filtrate was concentrated to about 14 L and flushed with toluene (~80 L) to remove excess morpholine. When final volume reached ~12 L, heptane (14 L) was added slowly at 60-70° C. The resulting slurry was cooled gradually to room temperature and aged for 3 h. It was then filtered and washed with heptane (12 L) and dry under nitrogen gave a slightly pink solid (6.26 kg, 97% pure, 98% yield). m.p.: 136° C. (DSC). $^1$H NMR (CDCl$_3$), δ 6.02 (d, J=3.2 Hz, 1H), 5.11 (br s, 1H), 4.62 (d, J=3.2 Hz, 1H), 4.58 (d, J=3.2 Hz, 1H), 3.9-3.5 (m, 8H), 1.51 (s, 3H), 1.35 (s, 3H). $^{13}$C NMR (methanol-d$_4$) δ 26.84, 27.61, 44.24, 47.45, 68.16, 77.14, 81.14, 86.80, 106.87, 113.68, 169.05.

6.3. Synthesis of 1-chloro-2-(4-ethoxybenzyl)-4-iodobenzene

A 2 L three-necked round bottom flask with mechanical stirrer, rubber septum with temperature probe and pressure-equalized addition funnel with gas bubbler was charged with 2-chloro-5-iodobenzoic acid (199.41 g, 0.706 mol), dichloromethane (1.2 L, KF=0.003 wt % water) and the suspension was set stirring at ambient temperature. Then N,N-dimethylformamide (0.6 mL, 1.1 mol %) was added followed by oxalyl chloride (63 mL, 0.722 mol, 1.02 equiv) which was added over 11 min. The reaction was allowed to stir at ambient overnight and became a solution. After 18.75 hours, additional oxalyl chloride (6 mL, 0.069 mol, 0.10 equiv) was added to consume unreacted starting material. After 2 hours, the reaction mixture was concentrated in vacuo to afford crude 2-chloro-5-iodobenzoyl chloride as a pale yellow foam which will be carried forward to the next step.

A jacketed 2 L three-necked round bottom flask with mechanical stirrer, rubber septum with temperature probe and pressure-equalized addition funnel with gas bubbler was charged with aluminum chloride (97.68 g, 0.733 mol, 1.04 equiv), dichloromethane (0.65 L, KF=0.003 wt % water) and the suspension was set stirring under nitrogen and was cooled to about 6° C. Then ethoxybenzene (90 mL, 0.712 mol, 1.01 equiv) was added over 7 minutes keeping internal temperature below 9° C. The resulting orange solution was diluted with dichloromethane (75 mL) and was cooled to −7° C. Then a solution of 2-chloro-5-iodobenzoyl chloride (≦0.706 mol) in 350 mL dichloromethane was added over 13 minutes keeping the internal temperature below +3° C. The reaction mixture was warmed slightly and held at +5° C. for 2 hours. HPLC analysis suggested the reaction was complete and the reaction was quenched into 450 mL pre-cooled (~5° C.) 2N aq. HCl with stirring in a jacketed round bottom flask. This quench was done in portions over 10 min with internal temperature remaining below 28° C. The quenched biphasic mixture was stirred at 20° C. for 45 min and the lower organic phase was washed with 1N aq. HCl (200 mL), twice with saturated aq. sodium bicarbonate (200 mL per wash), and with saturated aq. sodium chloride (200 mL). The washed extract was concentrated on a rotary evaporator to afford crude (2-chloro-5-iodophenyl)(4-ethoxyphenyl)methanone as an off-white solid (268.93 g, 99.0 area % by HPLC at 220 nm, 1.0 area % regioisomer at 200 nm, 98.5% "as-is" yield).

A jacketed 1 L three-necked round bottom flask with mechanical stirrer, rubber septum with temperature probe and gas bubbler was charged with crude (2-chloro-5-iodophenyl)(4-ethoxyphenyl)methanone (30.13 g, 77.93 mmol), acetonitrile (300 mL, KF=0.004 wt % water) and the suspension was set stirring under nitrogen and was cooled to about 5° C. Then triethylsilane (28 mL, 175.30 mmol, 2.25 equiv) was added followed by boron trifluoride-diethyletherate (24 mL, 194.46 mmol, 2.50 equiv) which was added over about 30 seconds. The reaction was warmed to ambient over 30 min and was stirred for 17 hours. The reaction was diluted with methyl tert-butyl ether (150 mL) followed by saturated aq sodium bicarbonate (150 mL) which was added over about 1 minutes. Mild gas evolution was noticed and the biphasic solution was stirred at ambient for 45 minutes. The upper organic phase was washed with saturated aq. sodium bicarbonate (100 mL), and with saturated aq. sodium chloride (50 mL). The washed extract was concentrated on a rotary evaporator to about one half of its original volume and was diluted with water (70 mL). Further concentration in vacuo at 45° C. was done until white prills formed which were allowed to cool to ambient while stirring. After about 30 minutes at ambient, the suspended solids were isolated by filtration, washed with water (30 mL), and were dried in vacuo at 45° C. After about 2.5 hours, this afforded 1-chloro-2-(4-ethoxybenzyl)-4-iodobenzene as a slightly waxy white granular powder (28.28 g, 98.2 area % by HPLC at 220 nm, 97.4% "as-is" yield).

6.4. Synthesis of (4-chloro-3-(4-ethoxybenzyl)phenyl)((3aS,5R,6S,6aS)-6-hydroxy-2,2-dimethyltetrahydrofuro[2,3-d][1,3]-dioxol-5-yl)methanone

To a solution of 1-chloro-2-(4-ethoxybenzyl)-4-iodobenzene (500 mg, 1.34 mmol) in THF (5.0 mL) was added i-PrMgCl (2.0M in THF, 1.0 mL, 2.00 mmol) at 0-5° C., and the mixture was stirred for 1.5 h at 0-5° C. A solution of (3aS,5R,6S,6aS)-6-hydroxy-2,2-dimethyltetrahydrofuro[2,3-d][1,3]dioxol-5-yl)(morpholino)methanone (146.5 mg, 0.536 mmol) in THF (1.0 mL) was added dropwise at 0-5° C. and the mixture was kept stirring for 1 h, warmed to 20° C. and stirred at 20° C. for 2 hours. The reaction was quenched with saturated aq $NH_4Cl$, extracted with MTBE, washed with brine. The organic layer was concentrated and the residue was purified by silica gel column chromatography to afford the desired ketone (178 mg, 76%) as a white solid. $^1H$ NMR ($CDCl_3$) δ 7.88 (dd, J=8.4, 2.0 Hz, 1H), 7.82 (d, J=2.0 Hz, 1H), 7.50 (d, J=8.4 Hz, 1H), 7.12 (d, J=8.4 Hz, 2H), 6.86 (d, J=8.4 Hz, 2H), 6.07 (d, J=3.2 Hz, 1H), 5.21 (d, J=3.2 Hz, 1H), 4.58 (d, J=3.2 Hz, 1H), 4.56 (d, J=3.2 Hz, 1H), 4.16 (d, J=7.2 Hz, 2H), 4.03 (q, J=7.2 Hz, 2H), 1.54 (s, 3H), 1.42 (t, J=7.2 Hz, 3H), 1.37 (s, 3H).

6.5. Alternative synthesis of (4-chloro-3-(4-ethoxybenzyl)phenyl)((3aS,5R,6S,6aS)-6-hydroxy-2,2-dimethyltetrahydrofuro[2,3-d][3,1]dioxol-5-yl)methanone To a 20 L reactor equipped with a mechanical stirrer, a temperature controller and a nitrogen inlet was charged with the iodide (3.00 kg, 8.05 mol) and THF (8 L, 4× to the morpholinoamide) at room temperature and cooled to −5° C. To the above solution was added dropwise a solution of i-PrMgCl in THF (Aldrich 2 M, 4.39 L, 8.82 mol) at −5° C. over 3 hours. This Grignard solution was used in the ketone formation below.

To a 50 L reactor equipped with a mechanical stirrer, a temperature controller, and a nitrogen inlet was charged the morpholinoamide (HPLC purity=97 wt %, 2.01 kg, 7.34 mol) and THF (11 L, 5.5×) at room temperature and stirred for 45 minutes at room temperature and for 15 minutes at 30° C. The homogeneous solution was then cooled to −25° C. To this solution was added a solution of t-BuMgCl in THF (Aldrich 1M, 7.32 L, 7.91 mol) at −25° C. over 3 hours. Then the above Grignard solution was added to this solution at −20 over 41 minutes. The resulting solution was further stirred at −20° C. before quench. The reaction mixture was added to 10 wt % aqueous $NH_4Cl$ (10 L, 5×) at 0° C. with vigorous stirring, and stirred for 30 minutes at 0° C. To this mixture was added slowly 6 N HCl (4 L, 2×) at 0° C. to obtain a clear solution and stirred for 30 minutes at 10° C. After phase split, the organic layer was washed with 25 wt % aq NaCl (5 L, 2.5×). Then the organic layer was concentrated to a 3× solution under the conditions (200 mbar, bath temp 50° C.). EtOAc (24 L, 12×) was added, and evaporated to a 3× solution under the conditions (150 mbar, bath temp 50° C.). After removed solids by a polish filtration, EtOAc (4 L, 2×) was added and concentrated to dryness (150 mbar, bath temp 50° C.). The wet cake was then transferred to a 50 L reactor equipped with a mechanical stirrer, a temperature controller and a nitrogen inlet. After EtOAc was added, the suspension was heated at 70° C. to obtain a 2.5× homogeneous solution. To the resulting homogeneous solution was added slowly heptane (5 L, 2.5×) at the same temperature. A homogeneous solution was seeded and heptane (15 L, 7.5×) was added slowly to a little cloudy solution at 70° C. After stirred for 0.5 h at 70° C., the suspension was slowly cooled to 60° C. and stirred for 1 h at 60° C. The suspension was then slowly cool to room temperature and stirred for 14 h at the same temperature. The crystals were collected and washed with heptane (8 L, 4×), dried under vacuum at 45° C. to give the desired ketone as fluffy solids (2.57 kg, 100 wt % by HPLC, purity-adjusted yield: 81%).

6.6. Synthesis of (2S,3S,4R,5S,6R)-2-(4-chloro-3-(4-ethoxybenzyl)phenyl)-6-(methylthio)tetrahydro-2H-pyran-3,4,5-triyl triacetate 1. TMSOTf, thiourea
2. MeI, i-Pr₂NEt To a solution of the ketone (4-chloro-3-(4-ethoxybenzyl) phenyl)((3aS,5R,6S,6aS)-6-hydroxy-2,2-dimethyltetrahydrofuro[2,3-d][1,3]dioxol-5-yl)methanone (114.7 g, 0.265 mol) in MeOH (2 L, 17×) was added CeCl$_3$.7H$_2$O (118.5 g, 1.2 equiv) and the mixture was stirred at 20° C. until all solids were dissolved. The mixture was then cooled to −78° C. and NaBH$_4$ (12.03 g, 1.2 equiv) was added in portions so that the temperature of the reaction did not exceed—70° C. The mixture was stirred at −78° C. for 1 hour, slowly warmed to 0° C. and quenched with saturated aq NH$_4$Cl (550 mL, 5×). The mixture was concentrated under vacuum to remove MeOH and then extracted with EtOAc (1.1 L, 10× x2) and washed with brine (550 mL, 5×). The combined organics were concentrated under vacuum to afford the desired alcohol as a colorless oil (crude, 115 g). To this colorless oil was added AcOH (650 mL) and H$_2$O (450 mL) and the mixture was heated to 100° C. and stirred for 15 hours. The mixture was then cooled to room temperature (20° C.) and concentrated under vacuum to give a yellow oil (crude, ~118 g). To this crude oil was added pyridine (500 mL) and the mixture was cooled to 0° C. Then, Ac$_2$O (195 mL, ~8.0 equiv) was added and the mixture was warmed to 20° C. and stirred at 20° C. for 2 h. The reaction was quenched with H$_2$O (500 mL) and diluted with EtOAc (1000 mL). The organic layer was separated and concentrated under vacuum to remove EtOAc and pyridine. The residue was diluted with EtOAc (1000 mL) and washed with aq NaHSO$_4$ (1N, 500 mL, ×2) and brine (300 mL). The organic layer was concentrated to afford the desired tetraacetate intermediate as a yellow foam (~133 g).

To a solution of tetraacetate (133 g, 0.237 mol assuming pure) and thiourea (36.1, 2.0 equiv) in dioxane (530 mL, 4×) was added trimethylsilyl trifluoromethanesulfonate (TMSOTf) (64.5 mL, 1.5 equiv) and the reaction mixture was heated to 80° C. for 3.5 hours. The mixture was cooled to 20° C. and MeI (37 mL, 2.5 equiv) and N,N-diisopropylethylamine (DiPEA) (207 mL, 5.0 equiv) was added and the mixture was stirred at 20° C. for 3 h. The mixture was then diluted with methyl tertiary-butyl ether (MTBE) (1.3 L, 10×) and washed with H$_2$O (650 mL, 5× x2). The organic layer was separated and concentrated under vacuum to give a yellow solid. To this yellow solid was added MeOH (650 mL, 5×) and the mixture was reslurried at 60° C. for 2 h and then cooled to 0° C. and stirred at 0° C. for 1 hour. The mixture was filtered and the cake was washed with MeOH (0° C., 70 mL, ×3). The cake was dried under vacuum at 45° C. overnight to afford the desired triacetate (2S,3S,4R,5S,6R)-2-(4-chloro-3-(4-ethoxybenzyl)phenyl)-6-(methylthio)tetrahydro-2H-pyran-3,4,5-triyl triacetate (88 g, 60% over 4 steps) as a pale yellow solid. $^1$H NMR (CDCl$_3$) δ 7.37 (d, J=8.0 Hz, 1H), 7.20 (dd, J=8.0, 2.0 Hz, 1H), 7.07 (m, 2H), 6.85 (m, 2H), 5.32 (t, J=9.6 Hz, 1H), 5.20 (t, J=9.6 Hz, 1H), 5.05 (t, J=9.6 Hz, 1H), 4.51 (d, J=9.6 Hz, 1H), 4.38 (d, J=9.6 Hz, 1 h), 4.04 (m, 2H), 2.17 (s, 3H), 2.11 (s, 3H), 2.02 (s, 3H), 1.73 (s, 3H), 1.42 (t, J=7.2 Hz, 3H).

6.7. Alternative synthesis of (2S,3S,4R,5S,6R)-2-(4-chloro-3-(4-ethoxybenzyl)phenyl)-6-(methylthio) tetrahydro-2H-pyran-3,4,5-triyl triacetate To a 50 L reactor under nitrogen atmosphere, 40 L MeOH was charged, followed with the ketone (2.50 kg, 5.78 mol) and CeCl$_3$.7H$_2$O (2.16 kg, 1.0 equiv). Methanol (7.5 L) was added as rinse (totally 47.5 L, 19×). A freshly prepared solution of NaBH$_4$ (87.5 g, 0.4 equiv) in aqueous 1N NaOH (250 mL) was added slowly (35 min) at 15-25° C. The mixture was then stirred for 15 min. HPLC analysis of the reaction mixture showed approximately 90:10 diastereomeric ratio. The reaction was quenched with 10 wt % aq NH$_4$Cl (2.5 L, 1×) and the mixture was concentrated under vacuum to 5×, diluted with water (10 L, 4×) and MTBE (12.5 L, 5×). The mixture was cooled to 10° C. and 6 N aq HCl was added until the pH of the mixture reached 2.0. Stirring was continued for 10 minutes and the layers were separated. The organic layer was washed with H$_2$O (5 L, 2×). The combined aqueous layer was extracted with MTBE (12.5 L, 5×). The combined organic layers were washed with brine (2.5 L, 1×) and concentrated under vacuum to 3×. MeCN (15 L, 6×) was added. The mixture was concentrated again to 10 L (4×) and any solid residue was removed by a polish filtration. The cake was washed with minimal amount of MeCN.

The organic filtrate was transferred to 50 L reactor, and a pre-prepared 20 mol % aqueous H$_2$SO$_4$ solution (61.8 mL 98% concentrated H$_2$SO$_4$ and 5 L H$_2$O) was added. The mixture was heated to 80° C. for 2 hours and then cooled to 20° C. The reaction was quenched with a solution of saturated aqueous K$_2$CO$_3$ (5 L, 2×) and diluted with MTBE (15 L, 6×). The organic layer was separated, washed with brine (5 L, 2×) and concentrated under vacuum to 5 L (2×). MeCN (12.5 L, 5×) was added and the mixture was concentrated to 7.5 L (3×).

The above MeCN solution of (3S,4R,5R,6S)-6-(4-chloro-3-(4-ethoxybenzyl)phenyl)tetrahydro-2H-pyran-2,3,4,5-tetraol was cooled to 10° C., added with dimethylaminopyridine (17.53 g, 2.5 mol %), followed by slow addition of acetic anhydride (3.23 L, 6.0 equiv) and triethylamine (5 L, 2×, 6.0 equiv) so that the temperature of the mixture was kept below 20° C. The reaction was then warmed to 20° C. and stirred for 1 hour and diluted with MTBE (15 L, 6×). The mixture was slowly quenched with water (7.5 L, 3×). The organic layer was separated and washed with saturated aqueous KHCO$_3$ (5 L, 2×), 1N NaHSO$_4$ (5 L, 2×), and brine (5 L, 2×) in sequence.

The organic layer was then concentrated under vacuum to 5 L (2×). MeCN (12.5 L, 5×) was added and the solution was concentrated to 7.5 L (3×) (KF=0.08%). Dioxane (12.5 L, 5×) was added and the solution was concentrated to 7.50 L (3×) (KF=0.02%). Any residual solid was removed by a polish filtration and the cake was washed with minimal amount of dioxane (500 mL).

To the above filtrate was added thiourea (880 g, 2.0 equiv) and TMSOTf (1.57 L, 1.5 equiv). The reaction mixture was heated to 80° C. for 3 hours (>97% conversion). The mixture was cooled to 20° C. and methyl iodide (541 mL, 1.5 equiv) and diethylisopropylamine (3.02 L, 3.0 equiv) were added and the mixture was stirred at 20° C. for 18 hours. An extra methyl iodide charge (90 mL, 0.25 equiv) was added and the mixture was stirred at 20° C. for 1 hours. The mixture was then diluted with MTBE (25 L, 10×) and washed with water (12.5 L, 5× x2). The organic layer was separated and concentrated under vacuum to ~5 L (2×). MeOH (12.5 L, 5×) was added and the mixture was concentrated to 5× to afford a slurry. The mixture was then heated at 60° C. for 1 hour and cooled to 0° C. and stirred at 0° C. for 1 hour. The mixture was filtered and the cake was washed with MeOH (0° C., 2.5 L, 1× x2, 1.0 L, 0.4×). The cake was dried under vacuum at 45° C. overnight to afford the desired triacetate (1.49 kg, 47% over 4 steps) as a pale yellow/off-white solid.

6.8. Synthesis of (2S,3R,4R,5S,6R)-2-(4-chloro-3-(4-ethoxybenzyl)phenyl)-6-(methylthio)tetrahydro-2H-pyran-3,4,5-triol To a slurry of (2S,3S,4R,5S,6R)-2-(4-chloro-3-(4-ethoxybenzyl)phenyl)-6-(methylthio)tetrahydro-2H-pyran-3,4,5-triyl triacetate (90.0 g, 0.164 mol) in MeOH (900 mL, 10×) was added NaOMe in MeOH (25 wt %, 18 mL, 0.2×) at 20° C. and the mixture was stirred at 20° C. for 2 hours until all solids disappeared. The mixture was then concentrated to 300 mL, added to H₂O (1 L) and stirred for 1 hour. The solid was filtered and washed with H₂O (100 mL, ×3) and the cake was dried under vacuum at 45° C. overnight to afford the desired methyl thiolate (67.0 g, 95%). $^1$H NMR (CDCl₃) δ 7.38 (d, J=8.4 Hz, 1H), 7.22 (m, 2H), 7.11 (d, J=8.8 Hz, 2H), 6.83 (d, J=8.8 Hz, 2H), 4.35 (d, J=9.6 Hz, 1H), 4.15 (d, J=9.6 Hz, 1H), 4.10-3.95 (m, 3H), 3.64 (t, J=8.8 Hz, 1H), 3.50 (m, 2H), 2.73 (br s, 3H), 2.17 (s, 3H), 1.40 (t, J=7.2 Hz, 3H).

6.9. Preparation of Crystalline Anhydrous (2S,3R,4R,5S,6R)-2-(4-chloro-3-(4-ethoxybenzyl)phenyl)-6-(methylthio)tetrahydro-2H-pyran-3,4,5-triol Form 1

Under slightly positive nitrogen pressure, to a 50 L reactor was charged MeOH (12 L) and the triacetate (1.70 Kg, 3.09 mol). Methanol (5 L) was added as a rinse. The slurry was then added NaOMe in MeOH (25 wt %, 340 mL, 0.2×) in 15 minutes at 20° C. and the mixture was stirred at 20° C. for 2 hours until all solids disappeared. To the mixture was added slowly water (25.5 L, 15×) in 45 minutes with 5 g seeding (DSC 123° C.). Solids crashed out and the mixture was stirred at 20° C. for 1 hour, cooled to 0° C. and stirred for 30 minutes. The solid was filtered and washed with water (1.7 L, 1×, ×2) and the cake was dried under vacuum at 45° C. overnight to afford the title compound (m.p.≈123° C. by DSC peak; 1.28 Kg, 97.7% yield).

6.10. Preparation of Crystalline Anhydrous (2S,3R,4R,5S,6R)-2-(4-chloro-3-(4-ethoxybenzyl)phenyl)-6-(methylthio)tetrahydro-2H-pyran-3,4,5-triol Form 2

Under slightly positive nitrogen pressure, to a 50 L reactor was charged MEK (2-butanone, 4 L) and (2S,3R,4R,5S,6R)-2-(4-chloro-3-(4-ethoxybenzyl)phenyl)-6-(methylthio)tetrahydro-2H-pyran-3,4,5-triol Form 1(1.49 Kg). MEK (3.45 L) was added as a rinse. The mixture was heated to 80° C. and heptane (14.9 L, 10×) was slowly added in 1.5 hours. Solids started to crash out and the mixture was charged heptane (14.9 L, 10×) in 6 h. The mixture was stirred at 80° C. for 15 hours. The mixture was cooled to 20° C. in 3 hours and stirred at 20° C. for 1 hour. The solids were filtered and the cake was washed with MEK/heptane (2.5:7.5, v/v, 1.49 L, 1× x2), dried under nitrogen for 12 hours and under vacuum at 50° C. for 24 hours to afford the title compound as a white solid (m.p.≈134° C. by DSC peak; 1.48 Kg, 98% recovery).

6.11. Alternative Preparation of Crystalline Anhydrous (2S,3R,4R,5S,6R)-2-(4-chloro-3-(4-ethoxybenzyl)phenyl)-6-(methylthio)tetrahydro-2H-pyran-3,4,5-triol Form 2

To a 250 L reactor was charged the triacetate (10 kg) and methanol (75 kg). Sodium methoxide (1.6 kg, 30% solution) was added with 5 kg methanol rinse. The mixture was stirred at room temperature for at least 2 hours or until the reaction was complete. Charcoal (Darco G-60, 1 kg) was added with 5 kg methanol rinse. This mixture was heated at 40° C. for 1 h, cooled to room temperature, and filtered through celite. The cake was washed with methanol (10 kg). Water (100 kg) was added and the mixture was concentrated under vacuum. MTBE (200 kg) and water (50 kg) were added and phases were split. The organic layer was washed with water (100 kg) and concentrated under vacuum. MEK (100 kg) was added and the same about of solvent was distilled under vacuum. This MEK addition and distillation was repeated to dry the solution. Enough MEK was added to produce a solution of (2S,3R,4R,5S,6R)-2-(4-chloro-3-(4-ethoxybenzyl)phenyl)-6-(methylthio)tetrahydro-2H-pyran-3,4,5-triol in 50 L MEK. This solution was polish filtered and heptane (100 L) was added at about 80° C. Form 2 seeds (0.1 kg) were added followed by slow addition of heptane (100 L) as 80° C. Heating was continued for 8 h more at 80° C., cooled to 20° C. over at least 3 hours, held at this temperature for at least 2 hours, filtered, and washed with MEK/heptane. The cake was dried at 50° C. under vacuum to afford the title compound as a white solid (6.6 kg, 86% yield).

6.12. Synthesis of (2S,3R,4R,5S,6R)-2-(4-chloro-3-(4-ethoxybenzyl)phenyl)-6-(methylsulfonyl)tetrahydro-2H-pyran-3,4,5-triol To a mixture of urea hydrogen peroxide (UHP, 92.34 g, 6.0 equiv) and phthalic anhydride (72.70 g, 3.0 equiv) was added MeCN (720 mL) and MeOH (180 mL). The mixture was stirred at 20° C. until all solids were dissolved. Then a solution of (2S,3S,4R,5S,6R)-2-(4-chloro-3-(4-ethoxybenzyl)phenyl)-6-(methylthio)tetrahydro-2H-pyran-3,4,5-triyltriacetate (90.00 g, 0.163 mol) in MeCN (540 mL, 6×) was added and the mixture was stirred at 20° C. for 7 hours. The mixture was diluted with EtOAc (900 mL, 10×) and washed with saturated aq NaHCO$_3$ (900 mL, 450 mL) and H$_2$O (450 mL). The organic layer was then concentrated under vacuum to give a white solid (~95 g). To the above white solid was added MeOH (900 mL) and then NaOMe in MeOH (25 wt %, 18 mL, 0.2×) and the mixture was stirred at 20° C. for 3 h until all the solids disappeared. The mixture was concentrated to 300 mL and slowly added to H$_2$O (1350 mL) with stirring. The stirring was continued for 1 hour. The solid was filtered and the cake was washed with H$_2$O (90 mL, ×2) and dried under vacuum at 45° C. overnight to afford the desired sulfone (71.4 g, 96%). $^1$H NMR (CDCl$_3$) δ 7.35 (d, J=8.4 Hz, 1H), 7.20 (m, 2H), 7.081 (d, J=8.8 Hz, 2H), 6.78 (d, J=8.8 Hz, 2H), 4.58 (br s, 1H), 4.51 (br s, 1H), 4.42 (d, J=9.6 Hz, 1H), 4.24 (d, J=9.6 Hz, 1H), 4.10-3.90 (m, 4H), 3.74 (m, 1H), 3.54 (m, 1H), 3.36 (br s, 1H), 2.81 (s, 3H), 1.37 (t, J=7.2 Hz, 3H).

All publications (e.g., patents and patent applications) cited above are incorporated herein by reference in their entireties.

What is claimed is:
1. A compound of the formula:

2. The compound of claim 1, which has an X-ray powder diffraction pattern with peaks at one or more of about 7.7, 11.9, 12.4, 16.9, 19.5, 19.9, 21.9, 23.2, 24.1, and/or 27.7 degrees 2θ.

3. The compound of claim 1, which has a melting point of about 156° C.

4. A compound of the formula:

5. A compound of the formula:

6. A compound the formula:

7. A compound of the formula:

8. The compound of claim 7, which is crystalline.

9. The compound of claim 8, which has an X-ray powder diffraction pattern with peaks at one or more of about 7.6, 13.2, 17.0, 17.4, 18.6, 19.5, 20.5, 20.8 and/or 23.2 degrees 2θ.

10. The compound of claim 8, which has a melting point of about 113° C.

11. A compound of the formula:

12. The compound of claim 11, which is crystalline.

13. The compound of claim 12, which has an X-ray powder diffraction pattern with peaks at one or more of about 9.0, 16.9, 17.6, 18.2, 18.4, 18.8 and/or 22.7 degrees 2θ.

14. The compound of claim 12, which has a melting point of about 136° C.

* * * * *